United States Patent
Wallace

(10) Patent No.: US 10,413,346 B2
(45) Date of Patent: Sep. 17, 2019

(54) SURGICAL CUTTING DEVICE

(71) Applicant: Mayo Foundation for Medical Education and Research, Rochester, MN (US)

(72) Inventor: Michael B. Wallace, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 221 days.

(21) Appl. No.: 15/245,449

(22) Filed: Aug. 24, 2016

(65) Prior Publication Data

US 2017/0056091 A1 Mar. 2, 2017

Related U.S. Application Data

(60) Provisional application No. 62/209,101, filed on Aug. 24, 2015.

(51) Int. Cl.
*A61B 18/08* (2006.01)
*A61B 17/32* (2006.01)
(Continued)

(52) U.S. Cl.
CPC .... *A61B 18/082* (2013.01); *A61B 17/320016* (2013.01); *A61B 17/32056* (2013.01);
(Continued)

(58) Field of Classification Search
CPC .. A61B 2018/00261; A61B 2018/0025; A61B 2017/320048; A61B 2017/32006; A61B 2017/320016; A61B 2017/00557; A61B 2017/22054; A61B 2017/22051; A61B 17/320725; A61B 17/32; A61B 2018/00595; A61B 2018/00285; A61B 2018/00601; A61M 25/1011; A61M 2025/1013
See application file for complete search history.

(56) References Cited

U.S. PATENT DOCUMENTS 4,445,892 A   5/1984  Hussein et al.
4,781,677 A   11/1988 Wilcox
(Continued)

FOREIGN PATENT DOCUMENTS

CN   202027752 U   11/2011
CN   202387089 U   8/2012
(Continued)

*Primary Examiner* — Eun Hwa Kim
*Assistant Examiner* — Catherine Premraj

(57) ABSTRACT

A surgical cutting tool includes a catheter, a first diametrically expandable member such as an inflatable balloon at a first location on the catheter, a second diametrically expandable member such as an inflatable balloon at a second location on the catheter that is distally spaced from the first expandable member, a cutting tool such as a cauterization tip extending between the first and second expandable members, and expanding structure such as a lumen for enabling the first and second expandable members to be actuated between a reduced diameter state and an expanded diameter state, and thereby move and position the cutting tool radially with respect to the catheter.

12 Claims, 4 Drawing Sheets

(51) Int. Cl.
*A61B 18/00* (2006.01)
*A61B 17/3205* (2006.01)
*A61B 17/00* (2006.01)

(52) U.S. Cl.
CPC ............... *A61B 2017/00557* (2013.01); *A61B 2017/32006* (2013.01); *A61B 2018/0025* (2013.01); *A61B 2018/00285* (2013.01); *A61B 2018/00595* (2013.01); *A61B 2018/00601* (2013.01)

(56) References Cited

U.S. PATENT DOCUMENTS

| | | | |
|---|---|---|---|
| 5,320,605 A | 6/1994 | Sahota | |
| 5,674,232 A | 10/1997 | Halliburton | |
| 5,904,679 A * | 5/1999 | Clayman | A61B 17/22 604/114 |
| 5,938,660 A * | 8/1999 | Swartz | A61B 18/1492 606/45 |
| 5,971,955 A | 10/1999 | Nap et al. | |
| 6,517,515 B1 | 2/2003 | Eidenschink | |
| 7,066,905 B2 | 6/2006 | Squire et al. | |
| 7,578,831 B2 | 8/2009 | Von Oepen et al. | |
| 7,658,744 B2 * | 2/2010 | Jackson | A61B 17/320725 606/159 |
| 8,372,034 B2 | 2/2013 | Levit et al. | |
| 8,469,925 B2 | 6/2013 | Rowe et al. | |
| 2006/0184191 A1 * | 8/2006 | O'Brien | A61B 17/320725 606/192 |
| 2009/0292241 A1 | 11/2009 | Von Oepen et al. | |
| 2015/0080933 A1 * | 3/2015 | Igov | A61B 17/320016 606/190 |
| 2015/0150572 A1 * | 6/2015 | Kumbhari | A61B 17/22032 604/506 |

FOREIGN PATENT DOCUMENTS

| | | |
|---|---|---|
| DE | 19900698 A1 | 7/2000 |
| EP | 2359893 A1 | 8/2011 |

* cited by examiner

SURGICAL CUTTING DEVICE

CROSS REFERENCE TO RELATED APPLICATION

This application claims the benefit of U.S. Provisional Application No. 62/209,101 filed on Aug. 24, 2015 and entitled Surgical Cutting Device, which is incorporated herein by reference in its entirety and for all purposes.

FIELD OF THE INVENTION

The invention relates generally to surgical instruments. Embodiments of the invention include intraluminal cutting devices.

BACKGROUND

Surgical procedures such as stricturoplasty and pyloroplasty are performed to remove tissues at narrowed regions within the lumens of organs and other body structures. Stricturoplasty, for example, is performed in response to scar tissue that has built up in a patient's intestinal wall from inflammatory bowel conditions such as Crohn's disease. The scar tissue causes a stricture or narrowing of the lumen in the bowel. Pyloroplasty is performed to widen the opening at the pylorus, a thick, muscular area in the lower part of the stomach, to enhance the ability of stomach contents to empty into the small intestine. Electrocautery devices are sometimes used to incise the obstructive tissue during procedures of these types. However, it can be difficult to control parameters such as the depth and length of the incision when using devices of these types for these procedures.

There remains, therefore, a need for improved intraluminal cutting devices. Such devices that are capable of effectively removing tissue, while enabling efficacious control over the depth and length of the incision, would be especially desirable.

SUMMARY

Embodiments of the invention include a surgical cutting tool and method. Embodiments of the cutting tool include a catheter, a first diametrically expandable member at a first location on the catheter, a second diametrically expandable member at a second location on the catheter that is distally spaced from the first expandable member, a cutting tool extending between the first and second expandable members, and expanding structure for enabling the first and second expandable members to be actuated between a reduced diameter state and an expanded diameter state, and thereby move and position the cutting tool radially with respect to the catheter.

Embodiments of the method include inserting the cutting tool into a lumen of a patient while the expandable members are in the reduced diameter state, positioning the first and second expandable members on opposite sides of an incision area such as an occlusion, actuating the expanding structure to (1) expand the first and second expandable members to the expanded diameter, (2) engage at least one and optionally both of expandable members with the lumen, and (3) urge the cutting tool into contact with tissues in the lumen, actuating the cutting tool to incise the tissue, actuating the expanding structure to retract the first and second expandable members to the reduced diameter state, and withdrawing the cutting tool from the lumen while the expandable members are in the reduced diameter state.

DETAILED DESCRIPTION

Figure 1A:
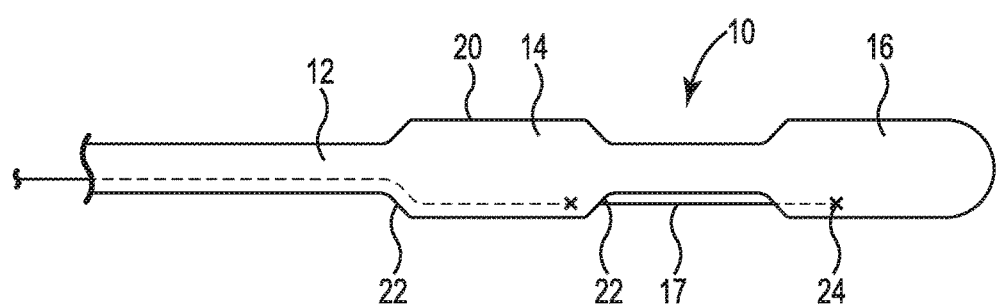
FIGS. 1A and 1B are illustrations of a surgical cutting tool in accordance with embodiments of the invention in reduced diameter and expanded diameter states, respectively.
Figure 1B:
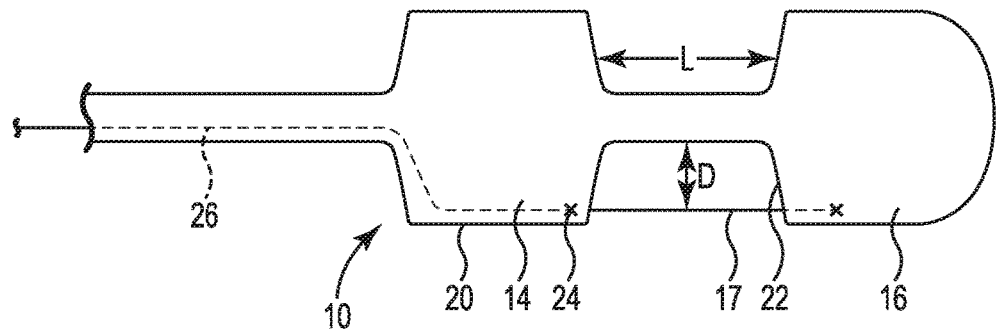

FIGS. 1A and 1B illustrate a distal portion of a surgical cutting tool 10 in accordance with embodiments of the invention. FIG. 1A shows the cutting tool 10 in a first, reduced diameter state that the device can take, for example, during insertion into and withdrawal from the patient's body. FIG. 1B shows the cutting tool 10 in a second, expanded diameter state that the device can take when it is operated to incise tissue. As shown, the tool 10 includes a catheter 12, a first or proximal diametrically expandable member such as balloon 14, a second or distal diametrically expandable member such as balloon 16, and a cutting tool such as cauterization tip 17. Balloons 14 and 16, which can be structures similar to those in convention angioplasty devices, are spaced apart along the longitudinal axis of the catheter 12 by a distance L, and are both coupled to a lumen 18 extending through the catheter. The lumen 18 is coupled to an inflation fluid source (not shown), and can function in a conventional manner as an expanding structure. When fluid from the source is delivered to balloons 14 and 16, they will expand from the reduced diameter state shown in FIG. 1A, to the expanded diameter state shown in FIG. 1B. Similarly, when fluid from the source is withdrawn, the balloons 14 and 16 will retract to the reduced diameter states shown in FIG. 1A. As shown, the balloons 14 and 16 have an outer surface portion 20, and side portions 22 that extend between the outer surface portions and catheter 12. The distance L defines a cutting length of the tool 10 in embodiments having a cauterization tip 17 that is operative over the distance L. Other embodiments have a cauterization tip 17 with an operative length that is less that the distance L between the balloons 14 and 16. Other embodiments of the invention have other types of diametrically expandable members (e.g., wire cages) and associated expanding structures.

Cauterization tip 17 extends between the balloons 14 and 16, and in the illustrated embodiment is fixedly attached to both of the balloons at radial and longitudinal locations by attachment structures 24 such as adhesive. In the illustrated embodiment, the cauterization tip 17 extends between side portions 22 of the balloons 14 and 16, adjacent the outer surface portions 20. A power cable 26, which can be coupled to a conventional cauterization controller (not shown) extends from the cauterization tip 17, and is located within the catheter 12 in the illustrated embodiment. In other embodiments (not shown), the power cable 26 can extend partially or wholly outside of the catheter 12. In other embodiments (not shown) the cauterization tip 17 extends between the outer surface portions 20 of one or both of the balloons 14 and 16. Because the cauterization tip 17 is fixed to one or both of balloons 14 and 16 at predetermined radial locations, when the balloons are actuated between the retracted and expanded states, the cauterization tip will move radially with respect to the catheter (while remaining at generally the same radial location on the balloons). Expanding the balloons 14 and 16 therefore moves and positions the cauterization tip 17 radially with respect to the catheter 12. The distance D by which the cauterization tip 17 extends from the catheter 12 when the balloons 14 and 16 are expanded effectively defines the cutting depth of the tool 10.

Figure 2A:
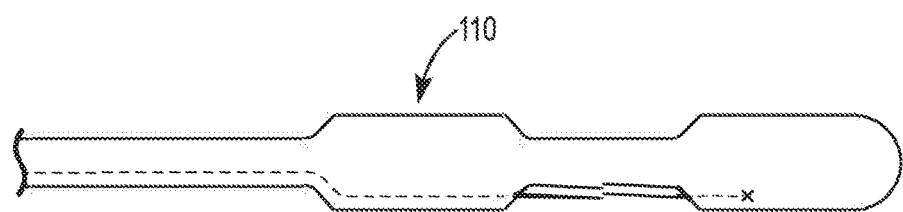
FIGS. 2A and 2B are illustrations of a surgical cutting tool in accordance with other embodiments of the invention in reduced diameter and expanded diameter states, respectively.
Figure 2B:
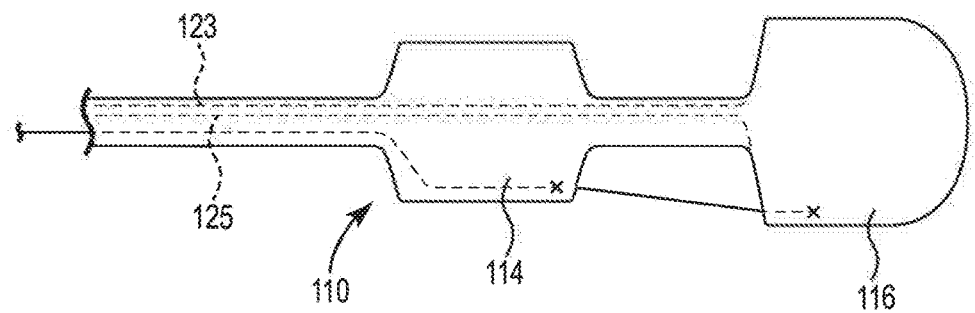

FIGS. 2A and 2B illustrate a surgical cutting tool 110 in accordance with other embodiments of the invention. Features of cutting tool 110 that are similar in structure and/or operation as those of cutting tool 10 are indicated by similar reference numbers. As shown, proximal balloon 114 is coupled to inflation lumen 125 and distal balloon 116 is coupled to inflation lumen 123. Balloons 114 and 116 can thereby be individually diametrically expanded, and, for example as shown in FIG. 2B, can be expanded to different diameters during surgical procedures. The cutting depth of cutting tool 110 can thereby be set to a varying profile over its cutting length. Other than these differences, cutting tool 110 can be the same as or similar to cutting tool 10.

Figure 3A:
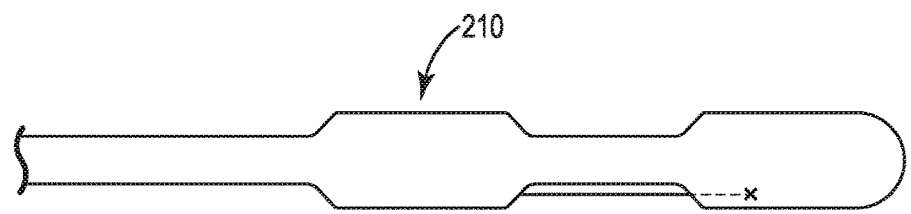
FIGS. 3A and 3B are illustrations of a surgical cutting tool in accordance with yet other embodiments of the invention in reduced diameter and expanded diameter states, respectively.
Figure 3B:
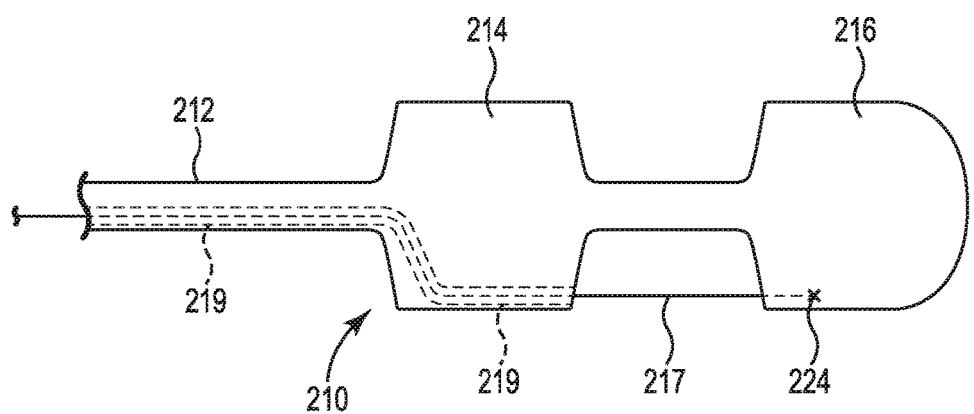

FIGS. 3A and 3B illustrate a surgical cutting tool 210 in accordance with yet other embodiments of the invention. Features of cutting tool 210, including catheter 212 and balloon 216, that are similar in structure and/or function to those of cutting tool 10 are indicated by similar reference numbers. As shown, the cauterization tip 217 extends through a lumen 219 in the proximal balloon 214, and is movable in the proximal balloon a longitudinal direction. This attachment structure 224 effectively fixes the cauterization tip 217 to the balloon 214 in the radial direction, but allows a surgeon to manipulate tension on the cauterization tip during surgical procedures. For example, the cauterization tip 217 can be provided with some slack to accommodate occlusive tissue during insertion of the tool 210, and pulled tight into engagement with the tissue to make the incision after insertion of the tool.

Figure 4A:
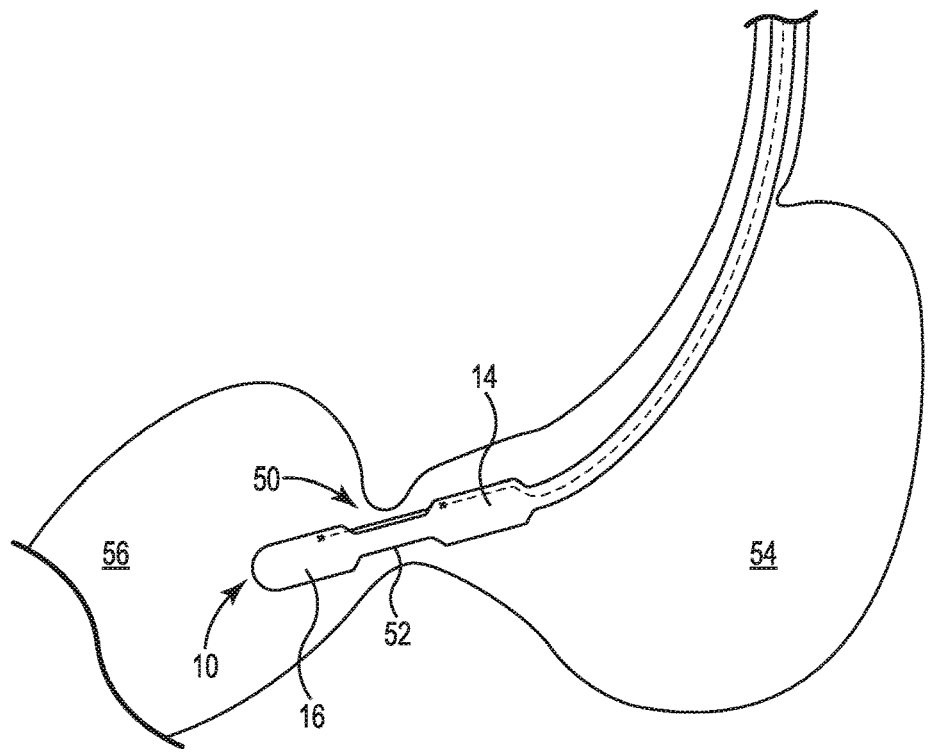
FIGS. 4A and 4B are illustrations of a surgical procedure that can be performed in accordance with embodiments of the invention using the cutting tools of the invention.
Figure 4B:
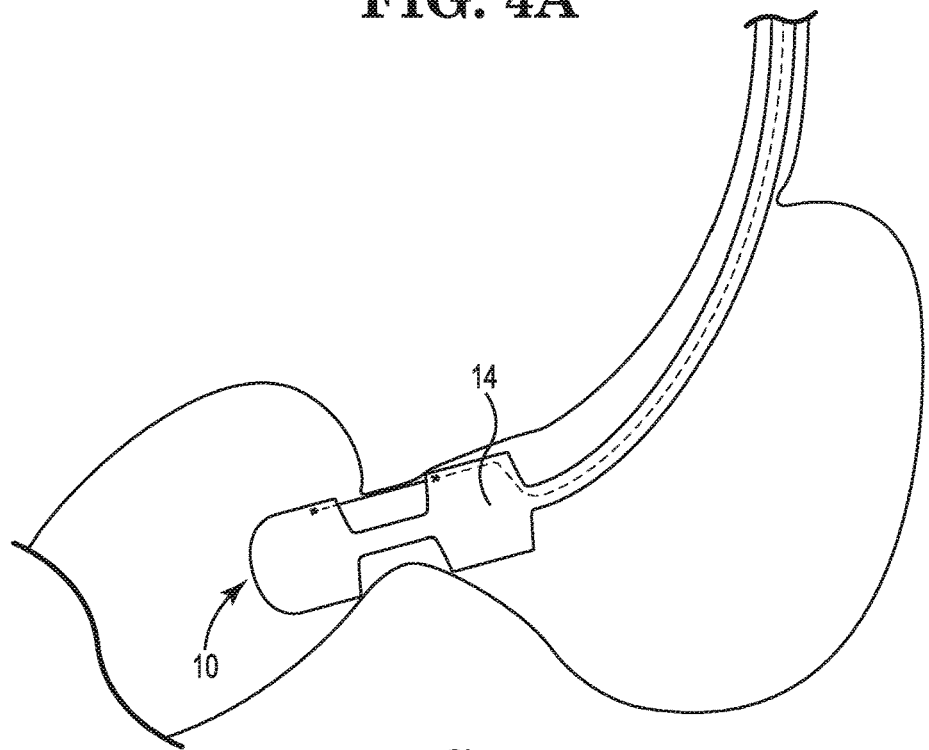

FIGS. 4A and 4B illustrate a pyloroplasty surgical procedure performed in accordance with embodiments of the invention. As shown in FIG. 4A, the lumen 52 adjacent the patient's pylorus 50 at the intersection of the stomach 54 and intestine 56 is occluded. A surgical tool in accordance with embodiments of the invention (tool 10 is shown for purposes of example), is interested through the stomach with the balloons 14 and 16 in the reduced diameter state. Balloons 14 and 16 are positioned on opposite sides of the pylorus 50, with the cauterization tip 17 adjacent to tissue to be incised. As shown in FIG. 4B, the balloons 14 and 16 are then inflated or otherwise expanded, with one or more of the balloons (e.g., balloon 14 in the illustrated embodiment) engaging the interior surface of the lumen 20 to position the cauterization tip 17 in contact with the tissue to be incised. Cauterization tip 17 can then be actuated to incise the tissue as shown in FIG. 4B. The tool 10 can be rotated or otherwise moved during this procedure to incise an area of tissue. The depth and length of the incision will be controlled by characteristics of the tool 10 and the amount by which the balloons 14 and 16 are expanded, as described above. Following the incision of the tissue, the balloons 14 and 16 can be actuated to deflate or otherwise return them to the reduced diameter state, and the tool 10 withdrawn from the patient. Other surgical procedures, such as stricturoplasty, can also be performed in a similar manner.

As described above, the cutting length and depth provided by tools in accordance with the invention can be defined by the structures of the tools. Tools in accordance with embodiments of the invention can therefore be configured with different cutting depths and/or lengths for different applications. Embodiments of the invention include sets of multiple tools configured with different cutting depths and/or lengths. Cutting tools in accordance with the invention enable efficacious surgical procedures.

Although the invention has been described with reference to preferred embodiments, those skilled in the art will recognize that changes can be made in form and detail without departing from the spirit and scope of the invention. In particular, features of the different embodiments can be combined in different combinations.

The invention claimed is:

1. A surgical cutting tool, including:
    a catheter;
    a first diametrically expandable member at a first location on the catheter, including:
        an outer surface portion configured to engage a lumen in a patient when the first expandable member is in an expanded diameter state; and
        side portions;
    a second diametrically expandable member at a second location on the catheter that is distally spaced from the first expandable member by a gap have a spacing length, including:
        an outer surface portion configured to engage the lumen in the patient when the second expandable member is in an expanded diameter state; and
        side portions;
    a cutting tool including a cauterization tip extending across the gap between the side portions of the first and second expandable members at a location spaced from the catheter by a distance defining a cutting depth and between the catheter and the outer surface portions of the first and second expandable members, and wherein the cutting tool is not located on the outer surface portions of the first and second expandable members; and
    expanding structure for enabling the first and second expandable members to be actuated between reduced diameter states and the expanded diameter states, and thereby move and position the cutting tool radially with respect to the catheter to the cutting depth.

2. The surgical cutting tool of claim 1 and further including distal fixing structure to attach the cutting tool to the second diametrically expandable member at a fixed radial and longitudinal location.

3. The surgical cutting tool of claim 2 and further including a proximal fixing structure to attach the cutting tool to the first expandable member at a fixed radial location while enabling longitudinal movement of the cutting tool on the first expandable member.

4. The surgical cutting tool of claim 3 wherein the proximal fixing structure includes a lumen.

5. The surgical cutting tool of claim 3 wherein the expanding structure includes first and second structures enabling the first and second expandable members to be independently actuated.

6. The surgical cutting tool of claim 5 wherein:
    the first and second expandable members are inflatable balloons; and
    the first and second expanding structures include lumens.

7. The surgical cutting tool of claim 2 and further including a proximal fixing structure to fixedly attach the cutting tool to the first diametrically expandable member at a fixed radial and longitudinal location.

8. The surgical cutting tool of claim 7 wherein the expanding structure includes first and second structures enabling the first and second expandable members to be independently actuated.

9. The surgical cutting tool of claim 8 wherein:
the first and second expandable members are inflatable balloons; and
the first and second expanding structures include lumens.

10. A set of more than one surgical cutting tools, wherein each of the more than one surgical cutting tools is in accordance with claim 1, each of the more than one surgical cutting tools having first and second expandable members spaced apart from one another by a gap having a spacing length to define a cutting length, wherein each of the more than one surgical cutting tools have different cutting lengths.

11. A set of more than one surgical cutting tools, wherein each of the more than one surgical cutting tools is in accordance with claim 1, each of the more than one surgical cutting tools having expandable members that are expandable to an expanded diameter state to define a cutting depth, wherein each of the more than one surgical cutting tools have different cutting depths.

12. A method for performing a surgical procedure using a cutting tool having a catheter, a first diametrically expandable member at a first location on the catheter, wherein the first expandable member includes an outer surface portion configured to engage a lumen in a patient when the first expandable member is in an expanded diameter state, and side portions, a second diametrically expandable member at a second location on the catheter that is distally spaced from the first expandable member by a gap having a spacing length, wherein the second expandable member includes an outer surface portion configured to engage the lumen in the patient when the first expandable member is in an expanded diameter state, and side portions, a cutting tool including a cauterization tip extending across the gap between the first and second expandable members at a location spaced from the catheter by a distance defining a cutting depth and between the catheter and the outer surface portions of the first and second expandable members, and wherein the cutting tool is not located on the outer surface portions of the first and second expandable members, and expanding structure for enabling the first and second expandable members to be actuated between reduced diameter states and the expanded diameter states, and thereby move and position the cutting tool radially with respect to the catheter to the cutting depth, the method including:
inserting the cutting tool into a lumen of a patient while the expandable members are in the reduced diameter states, and positioning the first and second expandable members on opposite sides of an incision area such as an occlusion;
actuating the expanding structure to (1) expand the first and second expandable members to the expanded diameter states, (2) engage the outer surface portions of at least one and optionally both of the first and second expandable members with the lumen, and (3) urge the cutting tool into contact with tissues in the incision area of the lumen and not portions of the lumen engaged by the outer surfaces of the first and second expandable members;
actuating the cutting tool to incise the tissue at the incision area to the cutting depth;
actuating the expanding structure to retract the first and second expandable members to the reduced diameter states; and
withdrawing the cutting tool from the lumen while the expandable members are in the reduced diameter states.

\* \* \* \* \*